(12) United States Patent
Konishi et al.

(10) Patent No.: US 10,366,617 B2
(45) Date of Patent: Jul. 30, 2019

(54) WALKING TRAINING APPARATUS AND WALKING TRAINING METHOD

(71) Applicant: TOYOTA JIDOSHA KABUSHIKI KAISHA, Toyota-shi (JP)

(72) Inventors: Kenta Konishi, Toyota (JP); Junji Matsuura, Toyoake (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 69 days.

(21) Appl. No.: 15/260,030

(22) Filed: Sep. 8, 2016

(65) Prior Publication Data

US 2017/0065849 A1    Mar. 9, 2017

(30) Foreign Application Priority Data

Sep. 8, 2015   (JP) ................................. 2015-176967

(51) Int. Cl.
*G09B 5/02* (2006.01)
*A61B 5/11* (2006.01)
(Continued)

(52) U.S. Cl.
CPC .............. *G09B 5/02* (2013.01); *A61B 5/0079* (2013.01); *A61B 5/1038* (2013.01); *A61B 5/112* (2013.01);
(Continued)

(58) Field of Classification Search
CPC ...... G09B 5/02; G09B 19/003; A61B 5/6828; A61B 5/0079; A61B 5/6895;
(Continued)

(56) References Cited

U.S. PATENT DOCUMENTS 6,231,527 B1 *   5/2001   Sol ....................... A61B 5/1038
                                                        348/143
2009/0124938 A1    5/2009   Brunner
(Continued)

FOREIGN PATENT DOCUMENTS

CN          103118647 A      5/2013
DE     10 2011 106 228 A1    1/2013
(Continued)

OTHER PUBLICATIONS

Brent Rose, "I Wore a Bionic Leg, and I Never Wanted to Take It Off Again", XP055338773, issued on Oct. 2013, pp. 1-6 , http://gizmodo.com/i-wore-a-bionic-leg-and-i-never-wanted-to-take-it-off-726536822.

*Primary Examiner* — Loan B Jimenez
*Assistant Examiner* — Shila Jalalzadeh Abyaneh
(74) *Attorney, Agent, or Firm* — Oblon, McClelland, Maier & Neustadt, L.L.P.

(57) ABSTRACT

A walking training apparatus includes a display disposed in front of a walking trainee, a first image capturing device for taking an image of the walking trainee from a viewpoint located above the walking trainee, and a display controller for controlling the display so that a target landing point together with an image of the walking trainee taken by the first image capturing device is displayed on a display screen of the display, the target landing point being a point on which the walking trainee should land his/her foot in a next step. The display controller controls the display so that a center line in addition to the target landing point of the foot are displayed on the display screen of the display, the center line indicating a center position in a left/right direction of the walking trainee.

5 Claims, 7 Drawing Sheets

(51) Int. Cl.
*A61B 5/103* (2006.01)
*A63B 22/00* (2006.01)
*A63B 22/02* (2006.01)
*G16H 20/30* (2018.01)
*G09B 19/00* (2006.01)
*A61B 5/00* (2006.01)
*A63B 69/00* (2006.01)
*A63B 71/06* (2006.01)
*A61H 1/02* (2006.01)
*A63B 21/00* (2006.01)
*A63B 24/00* (2006.01)

(52) U.S. Cl.
CPC .......... *A61B 5/1126* (2013.01); *A61B 5/6812* (2013.01); *A61B 5/6823* (2013.01); *A61B 5/6828* (2013.01); *A61B 5/6895* (2013.01); *A61H 1/024* (2013.01); *A61H 1/0262* (2013.01); *A63B 22/0023* (2013.01); *A63B 22/02* (2013.01); *A63B 69/0057* (2013.01); *A63B 71/0622* (2013.01); *G09B 19/003* (2013.01); *G16H 20/30* (2018.01); *A61B 5/1128* (2013.01); *A61B 5/4836* (2013.01); *A61B 2505/09* (2013.01); *A61B 2562/0219* (2013.01); *A61B 2562/0247* (2013.01); *A61H 2201/1207* (2013.01); *A61H 2201/1261* (2013.01); *A61H 2201/1284* (2013.01); *A61H 2201/1463* (2013.01); *A61H 2201/164* (2013.01); *A61H 2201/165* (2013.01); *A61H 2201/1676* (2013.01); *A61H 2201/5069* (2013.01); *A61H 2201/5079* (2013.01); *A63B 21/00181* (2013.01); *A63B 22/0235* (2013.01); *A63B 24/0087* (2013.01); *A63B 2024/0093* (2013.01); *A63B 2071/0625* (2013.01); *A63B 2071/0647* (2013.01); *A63B 2207/02* (2013.01); *A63B 2220/13* (2013.01); *A63B 2220/34* (2013.01); *A63B 2220/56* (2013.01); *A63B 2220/806* (2013.01); *A63B 2220/807* (2013.01); *A63B 2220/833* (2013.01); *A63B 2220/836* (2013.01)

(58) Field of Classification Search
CPC ... A61B 5/1126; A61B 5/6823; A61B 5/6812; A61B 5/112; A61B 5/1038; A61B 2562/0247; A61B 2562/0219; A61B 2505/09; A61B 5/4836; A61B 5/1128; A63B 69/0057; A63B 71/0622; A63B 22/0023; A63B 22/02; A63B 22/0235; A63B 2024/0093; A63B 2071/0625; A63B 24/0087; A63B 2071/0647; A63B 2207/02; A63B 2220/13; A63B 2220/34; A63B 2220/56; A63B 2220/806; A63B 2220/807; A63B 2220/833; A63B 2220/836; A63B 21/00181; A61H 1/024; A61H 1/0262; A61H 2201/5069; A61H 2201/165; A61H 2201/164; A61H 2201/1463; A61H 2201/5079; A61H 2201/1261; A61H 2201/1207; A61H 2201/1676; A61H 2201/1284; G06F 19/3481

See application file for complete search history.

(56) References Cited

U.S. PATENT DOCUMENTS

2012/0021873 A1* 1/2012 Brunner ............ A63B 22/0235
482/9
2013/0171601 A1* 7/2013 Yuasa ................ A61B 5/1114
434/258
2015/0003687 A1 1/2015 Utsunomiya et al.

FOREIGN PATENT DOCUMENTS

| JP | 2002-345785 A | | 12/2002 |
| JP | 2003-144580 A | | 5/2003 |
| JP | 2006-204730 A | | 8/2006 |
| JP | 2006204730 A | * | 8/2006 |
| JP | 2015-61579 A | | 4/2015 |
| WO | WO 2012/039467 A1 | | 3/2012 |

* cited by examiner

WALKING TRAINING APPARATUS AND WALKING TRAINING METHOD

CROSS-REFERENCE TO RELATED APPLICATIONS

This application is based upon and claims the benefit of priority from Japanese patent application No. 2015-176967, filed on Sep. 8, 2015, the disclosure of which is incorporated herein in its entirety by reference.

BACKGROUND

1. Field

The present disclosure relates to a walking training apparatus and a walking training method by which a user trains to walk.

2. Description of Related Art

A walking training apparatus including display means disposed in front of a person who is being trained to walk (hereinafter referred to as a "walking trainee"), image capturing means for taking an image of the walking trainee from a viewpoint located above the walking trainee, and display control means for displaying a target landing point of a foot of the walking trainee together with the image of the walking trainee taken by the image capturing means on a display screen of the display means has been known (see, for example, Japanese Unexamined Patent Application Publication No. 2006-204730).

Some walking trainees, such as patients having hemiplegia, tend to walk in a state where their bodies lean (i.e., incline) either to the left or to the right during walking trainings. However, the walking trainee himself/herself can hardly notice this left/right inclination of his/her body during the walking training. To cope with this, it is conceivable that, for example, an image of the walking trainee taken from a viewpoint located in front of or behind the walking trainee can be displayed on separately-provided display means so that the walking trainee can check the left/right inclination of his/her body. In such a case, however, the walking trainee has a troublesome task of checking the target landing point and the left/right inclination of his/her body in the different display means.

SUMMARY

The present disclosure has been made in view of the above-described problem and one of the main objects thereof is to provide a walking training apparatus and a walking training method for allowing a walking trainee to easily check a left/right inclination of his/her body by looking at a center line displayed near the target landing point of his/her foot.

To achieve the above-described object, a first exemplary aspect of the present disclosure is a walking training apparatus including: display means disposed in front of a walking trainee; first image capturing means for taking an image of the walking trainee from a viewpoint located above the walking trainee; and display control means for displaying a target landing point together with the image of the walking trainee taken by the first image capturing means on a display screen of the display means, the target landing point being a point on which the walking trainee should land his/her foot in a next step, in which the display control means displays a center line in addition to the target landing point of the foot on the display screen of the display means, the center line indicating a center position in a left/right direction of the walking trainee. According to this aspect, the walking trainee can easily check the left/right inclination of his/her body by looking at the center line displayed near the target landing point of his/her foot.

In this aspect, the walking training apparatus may further include inclination calculation mean for calculating an amount of a left/right inclination and a direction thereof of the body of the walking trainee based on information detected by at least one of a pressure sensor that detects a pressure on a sole of the foot of the walking trainee, an angular speed sensor attached to the walking trainee, second image capturing means for taking an image of the walking trainee from front of or behind the walking trainee, and the first image capturing means, and the display control means may display a mark indicating the amount of the inclination calculated by the inclination calculation means and the direction of the inclination or a counter-inclination direction adjacent to the center line on the display screen of the display means.

According to this aspect, since the walking trainee can visually recognize the amount and direction of the left/right inclination of his/her body just by looking at the mark displayed near the target landing point of the foot and the center line, the walking trainee can check the left/right inclination of his/her body more easily.

In this aspect, the walking training apparatus may further include at least one of sound output means for changing a sound output according to the inclination amount and the inclination direction calculated by the inclination calculation means, vibration means for changing a vibration given to the walking trainee, and optical output means for changing an optical output. According to this aspect, since the walking trainee can recognize the amount and direction of the left/right inclination of his/her body by the sound, the vibration, the light, and/or the like more intuitively, the walking trainee can check the left/right inclination of his/her body more easily.

To achieve the above-described object, another exemplary aspect of the present disclosure is a walking training method in which a target landing point is displayed together with an image of a walking trainee on a display screen of display means disposed in front of the walking trainee, the image of the walking trainee being taken by first image capturing means for taking the image of the walking trainee from a viewpoint located above the walking trainee, the target landing point being a point on which the walking trainee should land his/her foot in a next step, in which in addition to the target landing point of the foot, a center line is displayed on the display screen of the display means, the center line indicating a center position in a left/right direction of the walking trainee. According to this aspect, the walking trainee can easily check the left/right inclination of his/her body by looking at the center line displayed near the target landing point of his/her foot.

The present disclosure has been made in view of the above-described problem and can provide a walking training apparatus and a walking training method for allowing a walking trainee to easily check a left/right inclination of his/her body by looking at a center line displayed near the target landing point of his/her foot.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF THE EXEMPLARY EMBODIMENTS

First Exemplary Embodiment

A first exemplary embodiment according to the present disclosure is explained hereinafter with reference to the drawings.

Figure 1:
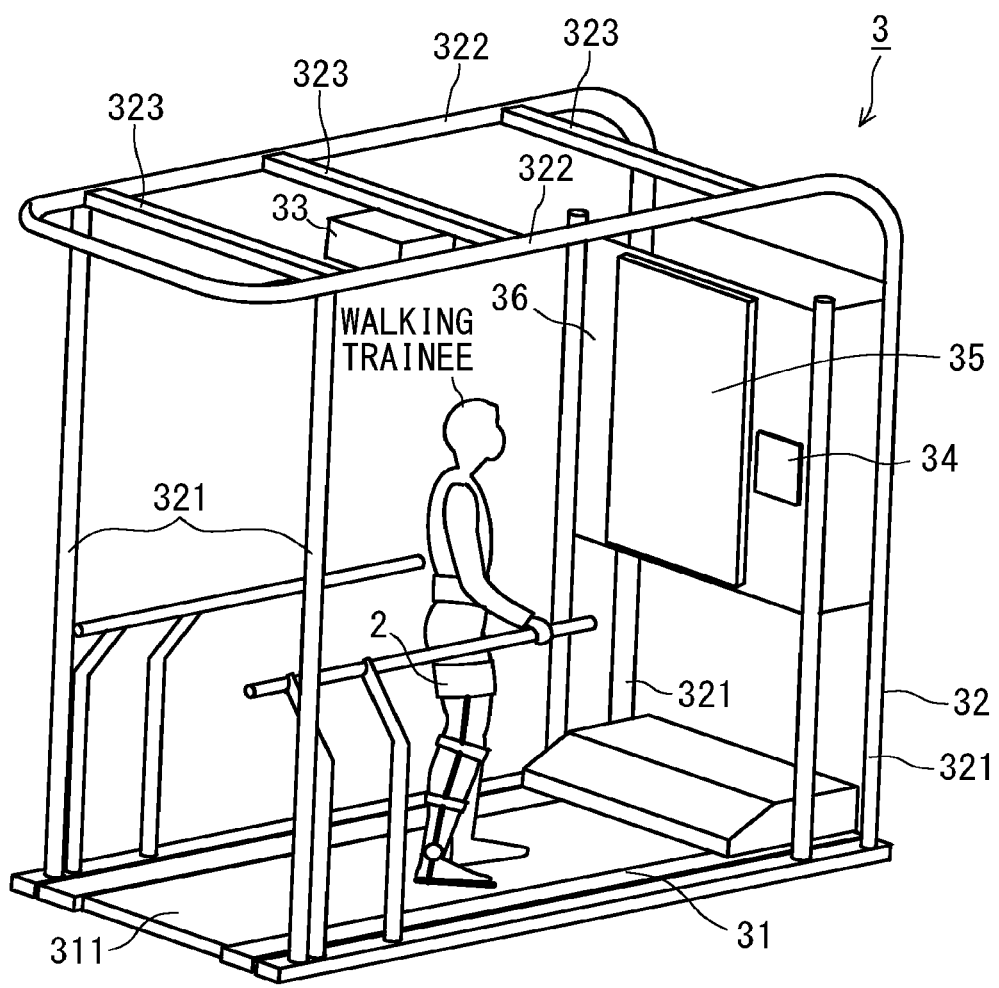
FIG. 1 is a perspective view showing a schematic configuration of a walking training apparatus according to a first exemplary embodiment of the present disclosure.
Figure 2:
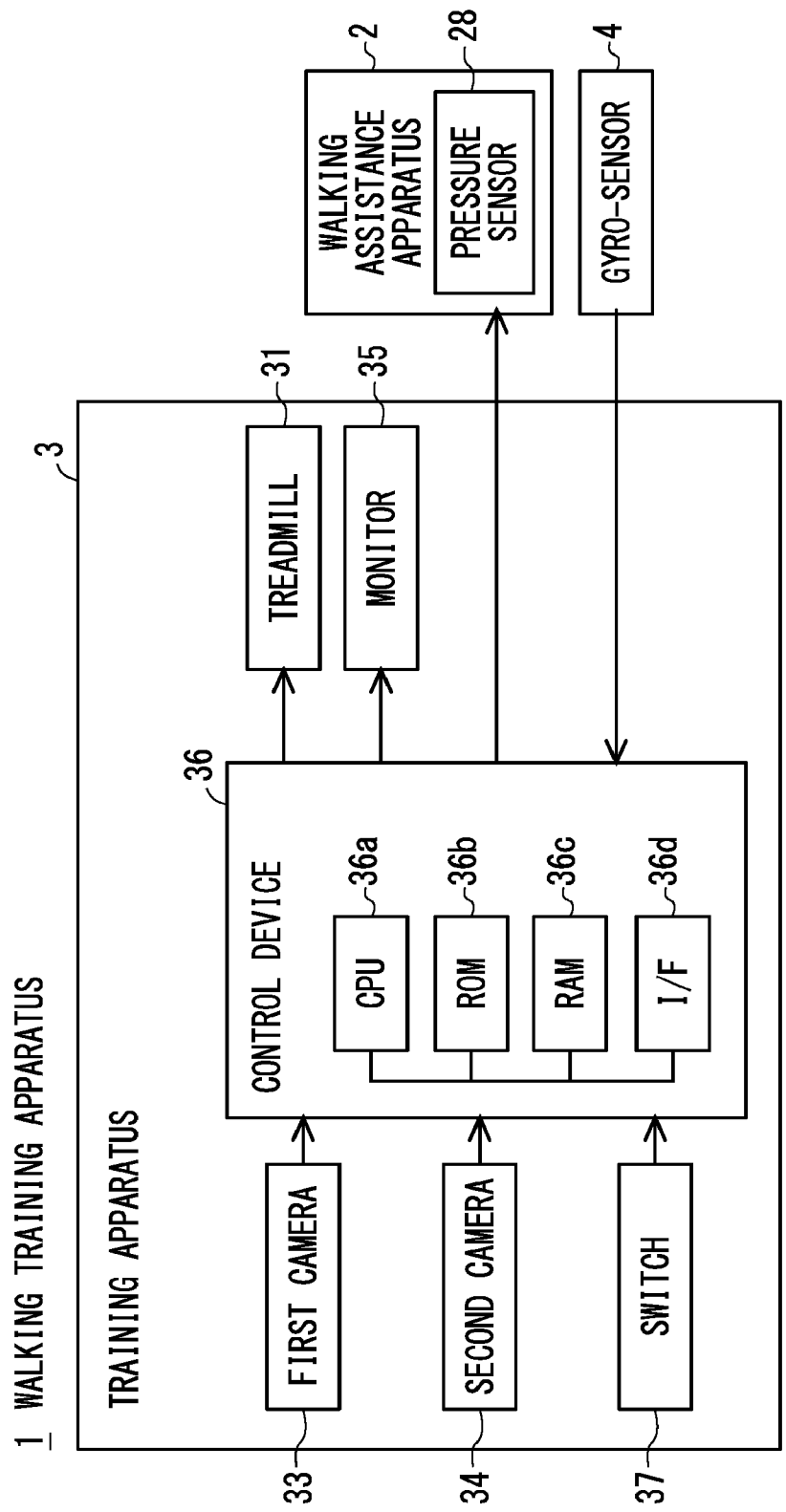
FIG. 2 is a block diagram showing a schematic system configuration of the walking training apparatus according to the first exemplary embodiment of the present disclosure.

FIG. 1 is a perspective view showing a schematic configuration of a walking training apparatus according to a first exemplary embodiment of the present disclosure. FIG. 2 is a block diagram showing a schematic system configuration of the walking training apparatus according to the first exemplary embodiment of the present disclosure. A walking training apparatus 1 according to the first exemplary embodiment is, for example, an apparatus by which a walking trainee such as a patient having hemiplegia caused by a stroke trains to walk. The walking training apparatus 1 includes a walking assistance apparatus 2 attached to a leg of the walking trainee, a training apparatus 3 by which the walking trainee trains to walk, and a gyro-sensor 4 attached to the walking trainee.

Figure 3:
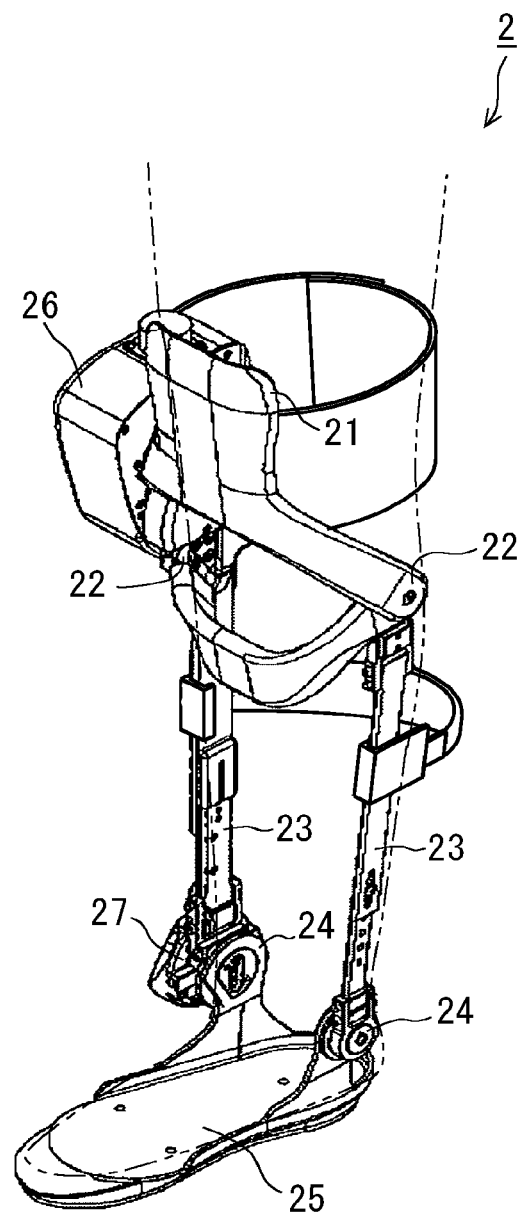
FIG. 3 is a perspective view showing a schematic configuration of a walking assistance apparatus according to the first exemplary embodiment of the present disclosure.

The walking assistance apparatus 2 is, for example, attached to a diseased leg of a walking trainee and assists walking of the walking trainee (FIG. 3). The walking assistance apparatus 2 includes an upper thigh frame 21, a lower thigh frame 23 connected to the upper thigh frame 21 through a knee joint part 22, a sole frame 25 connected to the lower thigh frame 23 through an ankle joint part 24, a motor unit 26 that rotationally drives the knee joint part 22, and an adjustment mechanism 27 that adjusts the movable range of the ankle joint part 24. Note that the above-described configuration of the walking assistance apparatus 2 is merely an example and the configuration of the walking assistance apparatus 2 is not limited to such an example. For example, the walking assistance apparatus 2 may include another motor unit that rotationally drives the ankle joint part 24.

A plurality of pressure sensors 28 is provided in the sole frame 25. The pressure sensors 28 are a specific example of the pressure detection means. Each of the pressure sensors 28 is, for example, a vertical pressure sensor that detects a vertical pressure exerted on the sole of the sole frame 25.

The upper thigh frame 21 is attached to the upper thigh of the leg of the walking trainee and the lower thigh frame 23 is attached to the lower thigh of the leg of the walking trainee. The motor unit 26 rotationally drives the knee joint part 22 according to the walking motion of the walking trainee and thereby assists the walking of the walking trainee. Note that the above-described configuration of the walking assistance apparatus 2 is merely an example and the configuration of the walking assistance apparatus 2 is not limited to such an example. Any walking assistance apparatus capable of being attached to the leg of the walking trainee and assisting walking of the walking trainee can be applied.

The gyro-sensor 4 is a specific example of the angular speed sensor. The gyro-sensor 4 is attached to, for example, the trunk of the walking trainee. The gyro-sensor 4 detects an inclination angular speed of the trunk of the walking trainee. Note that the gyro-sensor 4 may be attached to the head of the walking trainee.

The training apparatus 3 includes a treadmill 31, a frame main body 32, a first camera 33, a second camera 34, a monitor 35, and a control device 36. The treadmill 31 rotates a ring-shaped belt 311. The walking trainee gets on the belt 311 and walks on the belt 311 according to the movement of the belt 311. By doing so, the walking trainee trains to walk.

The frame main body 32 includes two pairs of pillar frames 321 vertically disposed on the treadmill 31, a pair of lengthwise frames 322 extending in the lengthwise direction and connected to respective pillar frames 321, and three crosswise frames 323 extending in the crosswise direction and connected to each of the lengthwise frames 322. Note that the configuration of the above-described frame main body 32 is not limited to this example.

The first camera 33 is a specific example of the first image capturing means. The first camera 33 is disposed, for example, in the crosswise frame 323 of the frame main body 32. The first camera 33 takes an image of the walking trainee walking on the treadmill 31 from a viewpoint located above the walking trainee. The first camera 33 then outputs the image of the walking trainee taken from the upper viewpoint to the control device 36.

The second camera 34 is a specific example of the second image capturing means. The second camera 34 is disposed, for example, in the front part of the frame main body 32. The second camera 34 takes an image of the walking trainee walking on the treadmill 31 from the front of the walking trainee. Alternatively, the second camera 34 may be disposed, for example, in the rear part of the frame main body 32 and takes an image of the walking trainee walking on the treadmill 31 from behind the walking trainee. The second camera 34 then outputs the image of the walking trainee taken from the front viewpoint or the rear viewpoint to the control device 36.

The monitor 35 is a specific example of the display means. The monitor 35 is disposed, for example, in the front part of the frame main body 32 and in front of the walking trainee. The monitor 35 is a liquid-crystal display device, an organic EL display device, or the like. The monitor 35 displays, for example, information such as an image of the walking trainee from the upper viewpoint, the front viewpoint, or the rear viewpoint, a training instruction (such as a target landing point on which the walking trainee should land his/her foot in the next step), a training menu, and training information (such as a walking speed and biometric information). For example, the monitor 35 is constructed as a touch panel and the walking trainee can enter various information items through the monitor 35.

The control device 36 is a specific example of the display control means. The control device 36 controls each of the monitor 35, the driving of the treadmill 31, and the walking assistance apparatus 2. For example, the control device 36 is formed by hardware mainly using a microcomputer including a CPU (Central Processing Unit) 36a that performs arithmetic processing, control processing, and so on, a ROM (Read Only Memory) 38b that stores an arithmetic program, a control program and so on to be executed by the CPU 36a, a RAM (Random Access Memory) 36c that stores various data and so on, and an interface unit (I/F) 36d that externally receives and outputs signals. The CPU 36a, the ROM 36b, the RAM 36c, and the interface unit 36d are connected with each other through a data bus or the like.

Figure 4:
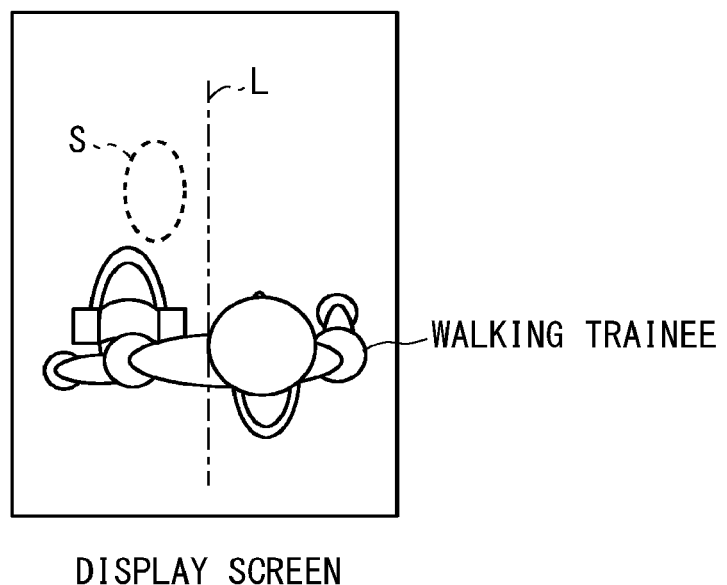
FIG. 4 shows an example of a target landing point of a foot and a center line displayed in a monitor.

The control device 36 calculates (or determines) a target landing point S on which the walking trainee should land his/her foot in the next step based on the image of the walking trainee from the upper viewpoint output from the first camera 33 (FIG. 4). For example, the control device 36 estimates the length of forward swinging of the leg of the walking trainee based on the moving speed of the belt 311 of the treadmill 31. Then, the control device 36 calculates the target landing point S of the foot of the walking trainee based on the image of the walking trainee from the upper viewpoint output from the first camera 33 and the estimated length of the swinging of the leg. Note that the above-described method for calculating a target landing point S is merely an example and the calculation method is not limited to this example.

The control device 36 displays the target landing point S of the foot of the walking trainee together with the image of the walking trainee from the upper viewpoint taken by the first camera 33 on the display screen of the monitor 35 during the walking training. The walking trainee walks so that his/her own foot lands on the target landing point S displayed in the monitor 35.

For example, some walking trainees, such as patients having hemiplegia, tend to walk in a state where their bodies are inclined either to the left or to the right during training. However, the walking trainee himself/herself can hardly notice the left/right inclination of his/her body during the walking training.

To cope with this, in the walking training apparatus 1 according to the first exemplary embodiment, the control device 36 displays a center line L indicating the center position in the left/right direction of the walking trainee in addition to the target landing point S of his/her foot on the display screen of the monitor 35 (FIG. 4). Therefore, the walking trainee can easily check the inclination of his/her body in the left/right direction by looking at the center line L displayed near the target landing point S of his/her foot.

For example, in the related art, an image of a walking trainee from a viewpoint located in front of or behind the walking trainee is displayed in a separately-provided monitor, and the walking trainee has a troublesome task of checking the target landing point and the left/right inclination of his/her body in the different monitors. In contrast to this, according to the walking training apparatus 1 in accordance with the first exemplary embodiment, as described above, as the walking trainee looks at the target landing point S of his/her foot on the screen of the monitor 35 located in front of him/her during a walking training, the center line L, which is displayed near the target landing point S, also comes into sight of the walking trainee. Therefore, the walking trainee can check the inclination of his/her body in the left/right direction without paying attention thereto.

The control device 36 calculates a center line L indicating the center position in the left/right direction of the walking trainee based on the upper-viewpoint image of the walking trainee output from the first camera 33. For example, the control device 36 determines the positions of the left and right feet of the walking trainee based on the image of the walking trainee from the upper viewpoint output from the first camera 33 and calculates a line extending from the center of the positions of the left and right feet in the front/rear direction (i.e., in the walking direction) as the center line L. Note that the above-described method for calculating a center line L is merely an example and the calculation method is not limited to this example. For example, the control device 36 may calculate a center line L based on information output from the gyro-sensor 4, the pressure sensors 28 of the walking assistance apparatus 2, or the second camera 34.

Note that the control device 36 may include a switch 37, and when it is switched on, the center line L may disappear from the display screen of the monitor 35 so that only the target landing point S of the foot is displayed on the display screen of the monitor 35. When a walking trainee trains to walk in the presence of a physical therapist, the physical therapist may give instructions about the left/right inclination of the body to the walking trainee. In such a case, the center line L disappears from the display screen of the monitor 35 when the above-described switch 37 is switched on, so that only the target landing point S of the foot is displayed on the display screen of the monitor 35. In this way, the walking trainee can do a walking training while concentrating only on the instructions about the left/right inclination of his/her body given by the physical therapist.

Figure 5:
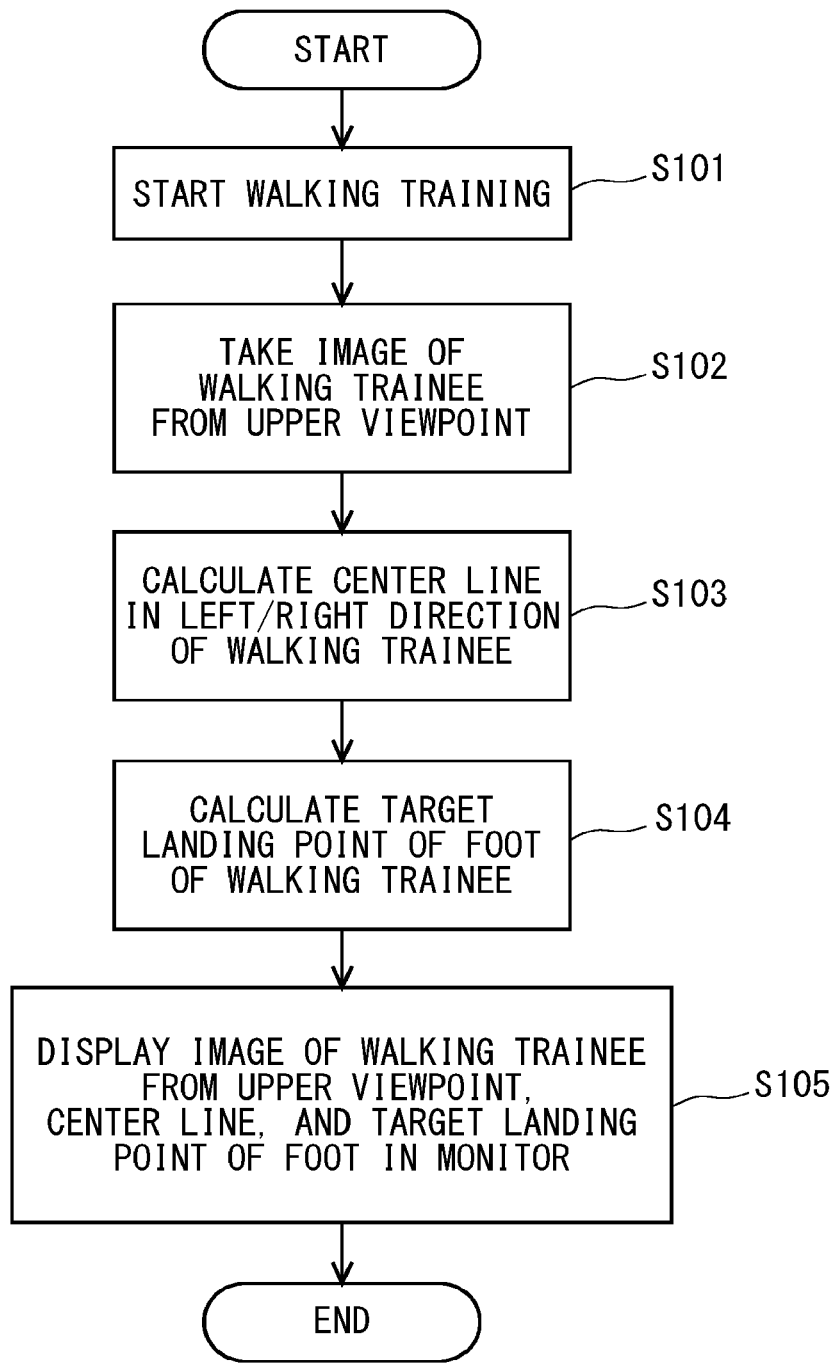
FIG. 5 is a flowchart showing a flow of a walking training method according to the first exemplary embodiment of the present disclosure.

FIG. 5 is a flowchart showing a flow of a walking training method according to the first exemplary embodiment of the present disclosure.

When walking training is started, the treadmill 31 is driven and a walking trainee starts walking on the treadmill 31 (step S101).

The first camera 33 takes an image of the walking trainee walking on the treadmill 31 from a viewpoint located above the walking trainee and outputs the image of the walking trainee taken by the first camera 33 to the control device 36 (step S102).

The control device 36 calculates a center line L indicating the center position in the left/right direction of the walking trainee based on the upper-viewpoint image of the walking trainee output from the first camera 33 (step S103).

The control device 36 calculates a target landing point S of the foot of the walking trainee based on the moving speed of the belt 311 of the treadmill 31 and the image of the walking trainee from the upper viewpoint output from the first camera 33 (step S104).

The control device 36 displays the target landing point S of the foot of the walking trainee and the center line L in the left/right direction of the walking trainee together with the image of the walking trainee from the upper viewpoint taken by the first camera 33 on the display screen of the monitor 35 (step S105) The walking trainee, while moving his/her feet according to their target landing points S displayed on the display screen of the monitor 35, checks the left/right inclination of his/her body by looking at the center line L displayed near the target landing point S of the foot in real time and thereby corrects the inclination. In this way, the walking trainee can, for example, correct his/her habit of inclining to the left/right by himself/herself during the walking training.

As described above, in the walking training apparatus 1 according to the first exemplary embodiment, in addition to the target landing point S of the foot, the center line L indicating the center position in the left/right direction of the walking trainee is displayed on the display screen of the monitor 35. Therefore, the walking trainee can easily check the inclination of his/her body in the left/right direction by looking at the center line L displayed near the target landing point S of his/her foot.

Second Exemplary Embodiment

Figure 6:
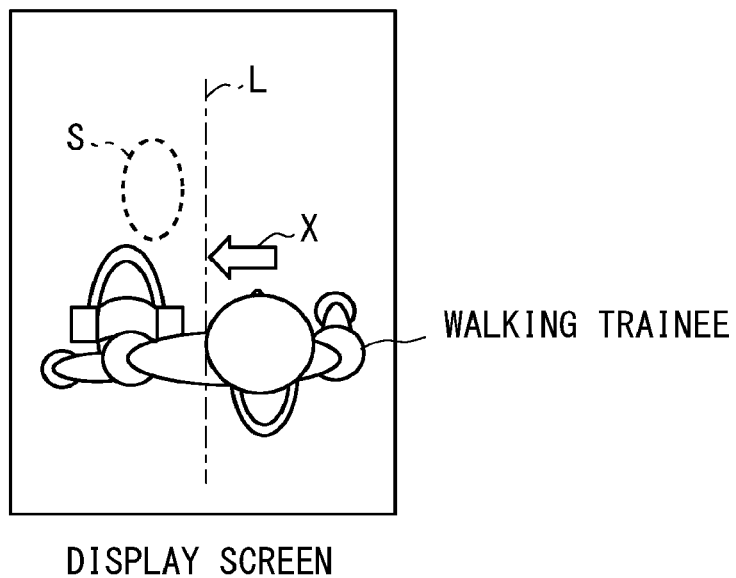
FIG. 6 shows an example of a target landing point of a foot, a center line, and a mark displayed in a monitor.

A control device 36 according to a second exemplary embodiment of the present disclosure calculates the amount of the left/right inclination of the body of the walking trainee and also calculates (i.e., determines) the inclination direction of the body of the walking trainee. Further, the control device 36 displays a mark X that indicates the calculated inclination amount (the amount of the inclination correction) and a counter-inclination direction (the direction of the inclination correction), i.e., a direction opposite to the inclination direction, adjacent to (or next to) the center line L in the left/right direction of the walking trainee on the display screen of the monitor 35 (FIG. 6). Alternatively, the control device 36 may display a mark X that indicates the calculated inclination amount (the amount of the inclination correction) and the inclination direction (the actual inclination direction) adjacent to (or next to) the center line L in the left/right direction of the walking trainee on the display screen of the monitor 35. In this way, the walking trainee can visually recognize the inclination amount of his/her body in the left/right direction and the inclination direction thereof just by looking at the mark X displayed near the target landing point S of his/her foot and the center line L, and thereby check the left/right inclination of his/her body more easily.

The control device 36 is a specific example of the inclination calculation means. The control device 36 calculates (or determines) the amount of the left/right inclination of the body of the walking trainee and the inclination direction thereof based on information detected by at least one of the pressure sensors 28 of the walking assistance apparatus 2, the gyro-sensor 4, the second camera 34, and the first camera 33.

Figure 7:
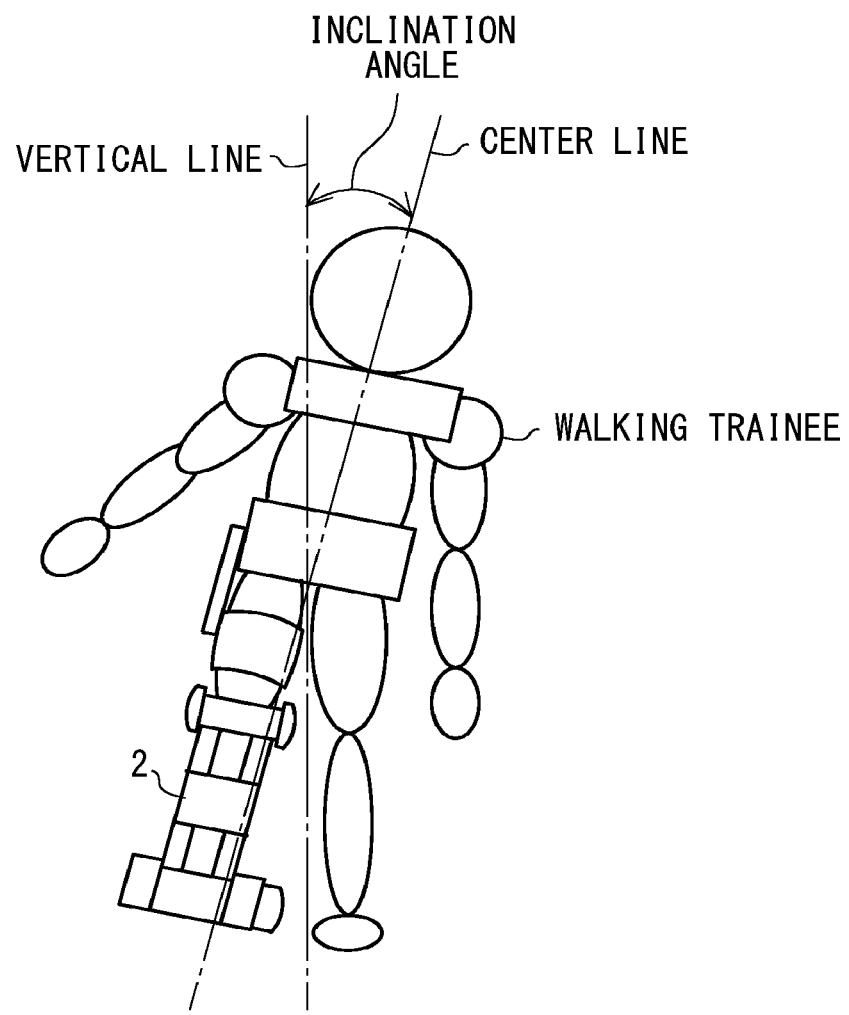
FIG. 7 shows an example of an inclination angle of a center line with respect to a vertical line from a viewpoint located in front of or behind a walking trainee.

For example, the control device 36 calculates (or determines) the amount of the left/right inclination of the body of the walking trainee and the inclination direction thereof based on the inclination angular speed of the trunk (or torso) of the walking trainee detected by the gyro-sensor 4. Alternatively, the control device 36 calculates the center line in the left/right direction of the trunk based on the image of the walking trainee from the front viewpoint or the rear viewpoint output from the second camera 34 (FIG. 7). Then, the control device 36 calculates the inclination direction and the inclination angle of the calculated center line with respect to the vertical line.

The control device 36 displays, for example, an arrow adjacent to (or next to) the center line in the left/right direction of the walking trainee as the mark X indicating the calculated inclination amount, and the calculated (or determined) inclination direction or the counter-inclination direction on the display screen of the monitor 35 (FIG. 6). The direction of this arrow indicates the inclination direction or the counter-inclination direction and the length of the arrow indicates the magnitude of the inclination amount. Note that the above-described mark is merely an example and the mark is not limited to this example. That is, any arbitrary mark can be applied, provided that the walking trainee can easily recognize the amount of the left/right inclination of the body of the walking trainee and the inclination direction thereof.

Note that by switching the switch 7, the mark X may be removed from the display screen of the monitor 35 and only the target landing point S of the foot and the center line L may be displayed on the display screen of the monitor 35. In this way, the walking trainee can train to walk while, for example, concentrating on instructions given by a physical therapist or the like.

As described above, according to the second exemplary embodiment, a mark X that indicates the amount of the left/right inclination of the body of the walking trainee and the inclination direction thereof is displayed adjacent to (or next to) the center line L in the left/right direction of the walking trainee on the display screen of the monitor 35. In this way, the walking trainee can easily check the left/right inclination of his/her body by looking at the mark X displayed near the target landing point S of his/her foot and the center line L.

Third Exemplary Embodiment

A control device 36 according to a third exemplary embodiment of the present disclosure may notify a walking trainee of at least one of the amount of the left/right inclination of the body of the walking trainee and the inclination direction thereof by a sound produced by a speaker. The speaker is a specific example of the sound output means.

For example, the control device 36 changes the frequency, the volume, the tone, and/or the like of the sound output from the speaker according to the amount of the left/right inclination of the body of the walking trainee and the inclination direction thereof. More specifically, the control device 36 raises the frequency or raises the volume of the sound output from the speaker as the amount of the left/right inclination the body of the walking trainee increases. The control device 36 outputs a sound from a right-side speaker when the body of the walking trainee is inclined to the right and outputs a sound from a left-side speaker when the body of the walking trainee is inclined to the left. Alternatively, the control device 36 may change the tone of the sound output from the speaker according to whether the body of the walking trainee is inclined to the right or to the left.

As described above, according to the third exemplary embodiment, the walking trainee is notified of at least one of the amount of the left/right inclination of his/her body and the inclination direction thereof by using a sound produced by a speaker. In this way, the walking trainee can recognize the inclination amount of his/her body in the left/right direction and the inclination direction thereof more intuitively, and thereby check the left/right inclination of his/her body more easily.

Note that the control device 36 may notify the walking trainee of at least one of the amount of the left/right inclination of the body of the walking trainee and the inclination direction thereof by a vibration produced by a vibration device. The vibration device is a specific example of the vibration means.

The control device 36 changes the frequency, the magnitude (i.e., the amplitude), and/or the like of the vibration produced by the vibration device according to the amount of the left/right inclination of the body of the walking trainee and the inclination direction thereof. More specifically, the control device 36 raises the frequency or raises the amplitude of the vibration of the vibration device as the amount of the left/right inclination of the body of the walking trainee increases. The control device 36 vibrates the right side of the walking trainee when the body of the walking trainee is inclined to the right and vibrates the left side of the walking trainee when the body of the walking trainee is inclined to the left.

The control device 36 changes the blinking frequency, the brightness, the color, and/or the like of light emitted from a lighting device according to the amount of the left/right inclination of the body of the walking trainee and the inclination direction thereof. The lighting device is a specific example of the optical output means.

More specifically, the control device 36 increases the blinking frequency or increases the brightness of the light emitted from the lighting device as the amount of the left/right inclination of the body of the walking trainee increases. The control device 36 turns on a right-side lighting device when the body of the walking trainee is inclined to the right and turns on a left-side lighting device when the body of the walking trainee is inclined to the left. Further, the control device 36 may notify the walking trainee of at least one of the amount of the left/right inclination of the body of the walking trainee and the inclination direction thereof by combining the speaker, the vibration device, and the lighting device in an arbitrary fashion.

Note that the present disclosure is not limited to the above-described exemplary embodiments, and various modifications can be made without departing from the spirit and scope of the present disclosure.

In the above-described exemplary embodiments, the walking assistance apparatus 2 does not necessarily have to be attached to the leg of the walking trainee.

In the above-described exemplary embodiments, the training apparatus 3 does not necessarily have to be equipped with the frame main body 32. In such a case, the monitor 35 and the first and second cameras 33 and 34 may be disposed (or mounted), for example, on the wall or the ceiling.

Although the user outfitted with the walking assistance apparatus 2 walks on the treadmill 31 in the above-described exemplary embodiment, the present disclosure is not limited to such a configuration. The present disclosure may be applied to a configuration in which a user outfitted with the walking assistance apparatus 2 walks on a stationary road surface and the monitor 35, the first and second cameras 33 and 34, and so on are moved according to the movement of the user.

From the invention thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A walking training apparatus comprising:
    a display disposed in front of a walking trainee;
    a first camera that takes an image of the walking trainee from a viewpoint located above the walking trainee; and
    a controller configured to control the display so that a target landing point together with the image of the walking trainee taken by the first camera is displayed on a display screen of the display, the target landing point being a point on which the walking trainee should land a foot of the walking trainee in a next step, wherein
    the controller is configured to
        determine positions of left and right feet of the walking trainee,
        calculate a center line extending from a center of the positions of the left and right feet in a front/rear direction, and
        control the display so that the center line in addition to the target landing point of the foot are displayed on the display screen of the display, the center line indicating a center position in a left/right direction of the walking trainee and indicating an inclination of a body of the walking trainee in the left/right direction.

2. The walking training apparatus according to claim 1, wherein the controller is further configured to calculate an amount of a left/right inclination and a direction thereof of the body of the walking trainee based on information detected by at least one of a pressure sensor that detects a pressure on a sole of the foot of the walking trainee, an angular speed sensor attached to the walking trainee, a second camera that takes an image of the walking trainee from front of or behind the walking trainee, and the first camera, and
    the controller is configured to control the display so that a mark indicating the calculated amount of the inclination and the direction of the inclination or a counter-inclination direction adjacent to the center line are displayed on the display screen of the display.

3. The walking training apparatus according to claim 2, further comprising at least one of a sound output device that outputs a sound, a vibration device that outputs a vibration, and an optical output device that outputs an optical output,
    wherein the controller is configured to change at least one of the sound output by the sound output device according to the inclination amount and the inclination direction, the vibration output by the vibration device, and the optical output which is outputted by the optical output device.

4. A walking training method comprising:
    displaying a target landing point together with an image of a walking trainee on a display screen of a display disposed in front of the walking trainee, the image of the walking trainee being taken by a first camera that takes the image of the walking trainee from a viewpoint located above the walking trainee, the target landing point being a point on which the walking trainee should land a foot of the walking trainee in a next step;
    determining positions of left and right feet of the walking trainee;
    calculating a center line extending from a center of the positions of the left and right feet in a front/rear direction; and
    displaying the center line on the display screen of the display, the center line indicating a center position in a left/right direction of the walking trainee and indicating an inclination of a body of the walking trainee in the left/right direction.

5. A walking training apparatus comprising:
    a display disposed in front of a walking trainee;
    a first sensor that takes an image of the walking trainee from a viewpoint located above the walking trainee; and
    a controller configured to control the display so that a target landing point together with the image of the walking trainee taken by the first sensor is displayed on a display screen of the display, the target landing point being a point on which the walking trainee should land a foot of the walking trainee in a next step, wherein
    the controller is configured to
        determine positions of left and right feet of the walking trainee,
        calculate a center line extending from a center of the positions of the left and right feet in a front/rear direction, and
        control the display so that the center line in addition to the target landing point of the foot are displayed on the display screen of the display, the center line indicating a center position in a left/right direction of the walking trainee and indicating an inclination of a body of the walking trainee in the left/right direction.

\* \* \* \* \*